(12) United States Patent
Watanabe et al.

(10) Patent No.: US 7,385,701 B2
(45) Date of Patent: Jun. 10, 2008

(54) STANDARD PLANE SAMPLE AND OPTICAL CHARACTERISTIC MEASUREMENT SYSTEM

(75) Inventors: Koji Watanabe, Edogawa-ku (JP); Norio Ishikawa, Osaka (JP); Masao Nakamuro, Takarazuka (JP)

(73) Assignee: Konica Minolta Sensing, Inc., Sakai-Shi (JP)

( * ) Notice: Subject to any disclaimer, the term of this patent is extended or adjusted under 35 U.S.C. 154(b) by 195 days.

(21) Appl. No.: 11/287,329

(22) Filed: Nov. 23, 2005

(65) Prior Publication Data

US 2006/0109458 A1  May 25, 2006

(30) Foreign Application Priority Data

Nov. 25, 2004  (JP) .............................. 2004-340763

(51) Int. Cl.
*G01J 3/46* (2006.01)

(52) U.S. Cl. ................. 356/402; 356/243.4; 356/243.5

(58) Field of Classification Search ................ 356/402, 356/445, 448, 243.8
See application file for complete search history.

(56) References Cited

U.S. PATENT DOCUMENTS

| 5,272,518 | A | * | 12/1993 | Vincent ....................... 356/405 |
| 5,982,501 | A | * | 11/1999 | Benz et al. .................. 356/446 |
| 2006/0024591 | A1 | * | 2/2006 | Itoh .............................. 430/5 |
| 2006/0073789 | A1 | * | 4/2006 | Horisaki ....................... 455/59 |

* cited by examiner

*Primary Examiner*—Fannie L Evans
*Assistant Examiner*—Abdullahi Nur
(74) *Attorney, Agent, or Firm*—Sidley Austin LLP

(57) ABSTRACT

A standard plane sample which supplies an optical characteristic measuring device with reference data. The standard plane sample including a sample portion that is measured by the optical characteristic measuring device to supply measurement data, and a recording medium that stores identification data for identifying a kind of the sample portion as well as reference data corresponding to the optical characteristic of the sample portion.

18 Claims, 11 Drawing Sheets

| ID | Item | Contents | |
|---|---|---|---|
| 1 | Sample identifier | 0000 | DK1 |
| 2 | Sample management number | 01234567 | DK2 |
| 3 | Shortest wavelength | 360 | DK3 |
| 4 | Wavelength pitch | 10 | DK4 |
| 5 | Number of pieces of data | 39 | DK5 |
| 6 | Measurement temperature | 23.0 | DK6 |
| 7 | Reflectance calibration data | 93.35, 95.15, 96.17, 96.98, 97.51, 97.58, 97.52, 97.35, 97.18, 97.03, 96.97, 96.82, 96.92, 96.95, 96.78, 96.74, 96.78, 96.81, 96.75, 96.59, 96.57, 96.56, 96.47, 96.40, 96.38, 96.28, 96.16, 96.08, 96.04, 95.98, 95.96, 95.95, 95.98, 95.99, 96.01, 95.93, 95.87, 95.82, 95.71 | DK7 |
| 8 | Calibration data | 2004/09/15 12:00:00 | DK8 |

Recalibration of white plate is recommended.
(The white plate becomes dirty due to use or deteriorates with time, and this changes the reflectance characteristics thereof. Accordingly, it is recommended to check/recalibrate regularly reflectance data in order to maintain measurement accuracy.)
Previous calibration date: * * * * (year)/* * (month)/* * (day)
　　　Contact address: * * * * * * *

| ID | Item | Color sample management information | |
|----|------|-------------------------------------|---|
| 11 | Sample identifier | 0001 | DK11 |
| 12 | Color sample name | Parts ABC, Red, forward right side portion | DK12 |
| 13 | Measurement date | 2004/09/27 15:00:00 | DK13 |
| 14 | Management range | $\Delta L^*=1.5$, $\Delta a^*=1.0$, $\Delta b^*=1.0$, $\Delta E^*ab=1.0$ | DK14 |
| 15 | Reflectance deviation range | Within 3% | DK15 |
| 16 | Shortest wavelength | 360 | DK16 |
| 17 | Wavelength pitch | 10 | DK17 |
| 18 | Number of pieces of data | 39 | DK18 |
| 19 | Measurement temperature | 23.0 | DK19 |
| 20 | Reflectance (color sample) data | 15.72 15.83 15.27 14.06 12.63 11.14<br>9.64 8.12 6.71 5.65 4.75 4.09<br>3.90 3.79 4.04 5.66 9.31 13.53<br>16.74 19.54 22.78 27.05 32.26 37.28<br>40.87 43.49 45.13 46.01 46.60 47.38<br>48.74 50.14 51.31 52.15 52.73 53.28<br>53.62 53.95 54.11 | DK20 |
| 21 | Colorimeter type | CM-2600d | DK21 |
| 22 | Body number | 12345678 | DK22 |
| 23 | Colorimeter version | V1.30 | DK23 |
| 24 | Measurement method (reflection/transmission) | Reflection | DK24 |
| 25 | Illumination light reception optical system | D/8 | DK25 |
| 26 | Measurement diameter | Φ8mm | DK26 |
| 27 | Regularly reflected light processing | SCE | DK27 |
| 28 | UV condition | UV Full | DK28 |
| 29 | Visual field | 10° | DK29 |
| 30 | Light source | D65 | DK30 |

| Measurement condition | calibration | reference color measurement | Measurement |
|-----------------------|-------------|------------------------------|-------------|

HG2

| | Determine/Not determine | Upper limit value | Lower limit value |
|---|---|---|---|
| ΔL* (C) | ✓ | 1.50 | −1.50 |
| Δa* (C) | ✓ | 1.50 | −1.50 |
| Δb* (C) | ✓ | 1.50 | −1.50 |
| ΔE*ab (C) | ✓ | 1.00 | |

STANDARD PLANE SAMPLE AND OPTICAL CHARACTERISTIC MEASUREMENT SYSTEM

CROSS-REFERENCE TO RELATED APPLICATION

This application is based on Japanese Patent Application No. 2004-340763 filed in Japan on Nov. 25, 2004, the entire content of which is hereby incorporated by reference.

BACKGROUND OF THE INVENTION

1. Field of the Invention

The present invention relates to a standard plane sample (also referred to as a standard plane sample for measuring device calibration, a specimen sample, or a reference plane sample) for supplying a measuring device with the reference data of the optical characteristic in an apparatus that measures the optical characteristic of a sample, and an optical characteristic measurement system in which such a standard plane sample and a measuring device are used as a set.

Specifically, the present invention relates to a standard color sample such as a standard white plate or color sample for supplying a calorimeter with reference data and a colorimetry system where such a standard color sample and a calorimeter are used as a set, or to a standard gloss sample such as a standard gloss sample or gloss specimen for supplying a glossmeter with reference data and a gloss measurement system in which such a standard gloss sample and a glossmeter are used as a set.

2. Description of the Related Art

In recent years, the importance of the color conditioning of products has come to be recognized in the fields of coating, molding, printing, fabric and the like. For this reason, measurement of the optical characteristic value such as measurement of the colors of products by use of a calorimeter is frequently performed in factories and the like.

In a case where a calorimeter is used, before measurement of the sample (object) to be measured is performed, calibration (user calibration) of the calorimeter is performed by use of a standard color sample, for example a standard white plate (hereinafter, referred to as white plate), annexed to the calorimeter.

Conventionally, the white plate is offered together with the calorimeter by the manufacturer. Normally, the white plate comes with calibration data or reference data obtained by actually measuring the reflectance (spectral reflectance) thereof. The calibration data is offered as printed matter such as paper, or as electric data stored in a storage medium such as a CD-ROM, a flexible disk or a memory card.

In order to input the calibration data of the white plate into the calorimeter, the data may be transferred from the storage medium every measurement. However, since this is onerous, normally, a nonvolatile memory is mounted in the calorimeter and the data is inputted when the colorimeter is purchased or when recalibration (value re-assignment, manufacturer calibration) of the white plate is-performed. Although the calibration data stored in the nonvolatile memory is, basically, not lost even when the colorimeter is turned off, it is necessary to input the calibration data again, for example, when the backup battery is exhausted.

The calibration using the white plate is to actually measure the reflectance (spectral reflectance) of the white plate. The calorimeter compares the actually measured value (actual measurement data) with the already read and stored calibration data (reflectance data) to calculate the correction coefficient, and multiplies the measurement data of the sample obtained thereafter by this correction coefficient. By such a calibration processing, the degradation in measurement accuracy due to fluctuations in the characteristic of the light source incorporated in the calorimeter can be suppressed.

Moreover, as the standard plane sample, some colorimetry applications use an arbitrary color sample (color tile, etc.) as well as the white plate.

While one calorimeter and one white plate constitute a set, when a plurality of calorimeters are provided, there are cases where which calorimeter and white plate constitute a set is uncertain. If a calorimeter is combined with a wrong white plate, the white plate not corresponding to the stored calibration data is actually measured in the calorimeter, so that an accurate correction coefficient cannot be obtained and accurate measurement cannot be performed also in this case.

Moreover, since inputting the calibration data into the colorimeter is not a frequency performed operation, the user has to look for the storage medium storing the calibration data when the operation is necessary, and there may be cases where the user cannot find the storage medium.

To cope with this problem, a colorimeter has conventionally been proposed in which a reference plate (white plate) for calibration is provided in the calorimeter and a measuring head is provided so as to be movable between the measurement position and the calibration position. That is, according to this calorimeter, at the time of the calibration, the measuring head is situated in the position of the reference plate for calibration inside the body, and at the time of the measurement of the object, the measuring head is moved to the position of the sample outside the body. By this, the calibration of white, R, G and B is automatically executed. By incorporating the white plate for calibration in the body, the white plate and the colorimeter can be integrally managed, so that it never occurs that a calorimeter is combined with a wrong white plate even when a plurality of calorimeters are provided.

The same problem as that of the above-described colorimetry system arises in the gloss measurement system. In a case where a glossmeter is used, before measurement of the sample (object) to be measured is performed, calibration (user calibration) of the glossmeter is performed by use of a standard gloss sample annexed to the glossmeter, and also with this standard gloss sample, the same problem as that of the standard white plate in the case of the calorimeter arises, that is, the following problem arises: the problem in the management of the standard gloss sample and the reference data thereof caused because the standard gloss sample and the reference data thereof are separately offered or the miscombination of the glossmeter and the standard gloss sample when the user has a plurality of glossmeters.

However, in the conventional calorimeter, since the white plate is integrally attached inside the calorimeter, the maintenance of the white plate is cumbersome. That is, the white plate becomes dirty due to use or deteriorates with time and this changes the reflectance thereof. While the amount of change differs according to the condition of use or the condition of storage, it is recommended to perform calibration (manufacturer calibration) every one to two years. In the calibration, the white plate is sent to the manufacturer, and the manufacturer re-measures the reflectance of the white plate, confirms the calibration data and performs recalibration (value re-assignment). This task is onerous in the structure of the calorimeter of the patent document 1.

Further, users are not sufficiently aware of the calibration of the white plate, and in many cases, even when the time when the calibration of the white plate must be performed comes, the user does not notice it and misses the opportunity of the calibration. Moreover, even when the user notices it, there are cases where the user cannot seize an opportunity to send the white plate for calibration and misses the opportunity. Consequently, there is a possibility that a condition where no calibration is performed continues over a long period of time.

SUMMARY OF THE INVENTION

A principal object of the present invention is to provide a standard plane sample and an optical characteristic measurement system capable of always performing appropriate calibration.

Another object of the present invention is to provide a standard plane sample and an optical characteristic measurement system in which a miscombination of the standard color sample such as the white plate and the reference data never occurs.

Yet another object of the present invention is to provide a calorimeter capable of easily reading the reference data.

Still another object of the present invention is to provide a standard plane sample and an optical characteristic measurement system capable of performing the calibration (manufacturer calibration) of the standard color sample at appropriate timing.

The above-mentioned objects of the present invention are attained by providing the following standard plane sample:

A standard plane sample for supplying an optical characteristic measuring device with reference data, comprising:

a sample portion that is measured by the optical characteristic measuring device to supply actual measurement data; and a recording medium that stores identification data for identifying a kind of the sample portion as well as reference data corresponding to an optical characteristic of said sample portion.

Moreover, the above-mentioned objects of the present invention are also attained by providing the following optical characteristic measurement system:

An optical characteristic measurement system for measuring an optical characteristic of an object, comprising:

a standard plane sample comprising:
  a sample portion that is measured by the optical characteristic measuring device to supply measurement data;
  a recording medium that stores identification data for identifying a kind of the sample portion as well as reference data corresponding to the optical characteristic of the sample portion; and
  a communication portion that performs data transmission with the optical characteristic measuring device; and the optical characteristic measuring device comprising:
  a measuring portion that measures the object;
  a reading and writing portion that performs data transmission with the standard plane sample through the communication portion of the standard plane sample, and receives data stored in the recording medium of the standard plane sample from the communication portion of the standard plane sample;
  a sample data storage portion that stores the data received by the reading and writing portion;
  a comparator that compares, when it is determined that the standard plane sample is a standard plane sample for calibration based on the identification data, measurement data obtained upon measuring the sample portion of the standard plane sample by the measuring portion with the reference data received from the standard plane sample;
  a correction coefficient calculator that generates correction coefficient data based on a difference between the measurement data of the sample portion and the reference data; and
  a measurement corrector that generates corrected measurement data by applying the correction coefficient data on the measurement data obtained upon measurement of the object by the measuring portion.

These and other objects, advantages and features of the invention will become apparent from the following description thereof taken in conjunction with the accompanying drawings, which illustrate specific embodiments of the invention.

BRIEF DESCRIPTION OF DRAWINGS

These and other objects, advantages and features of the invention will become apparent from the following description thereof taken in conjunction with the accompanying drawings in which:

FIG. 3 is a view showing an example of the data stored in a storage medium of a standard color sample;

FIG. 4 is a view showing an example of a recalibration urging message;

FIG. 9 is a view showing an example of the data stored in a storage medium of a standard color sample;

FIG. 10 is a view showing an example of a colorimetry trigger screen;

DESCRIPTION OF THE PREFERRED EMBODIMENTS

First Embodiment

In the first embodiment, taking up a colorimeter as an example of the optical characteristic measuring device, an example of a system for always performing appropriate calibration of the calorimeter with reliability will be described.

Figure 1:
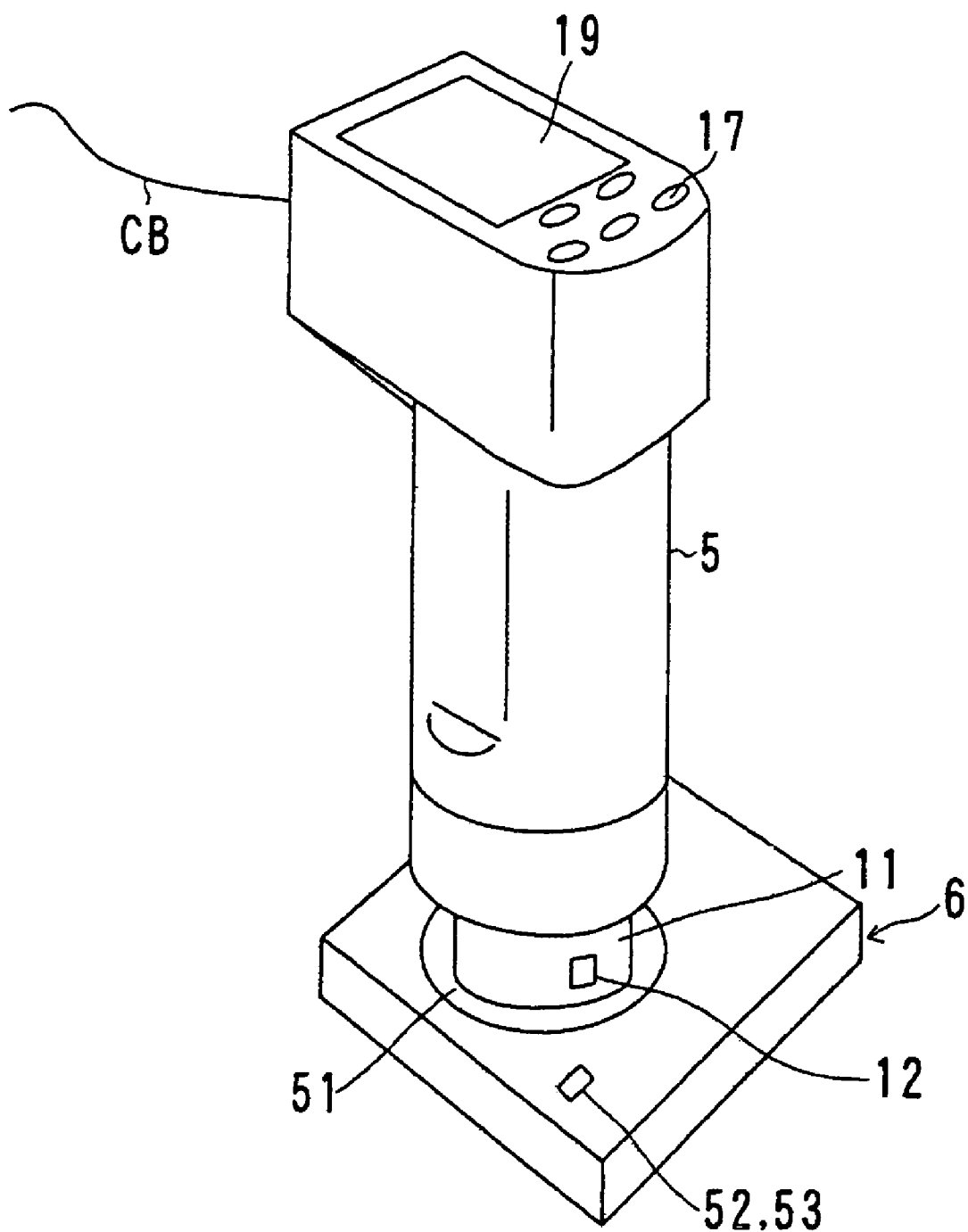
FIG. 1 is a perspective view showing the appearance of a colorimetry system according to a first embodiment of the present invention.
Figure 2:
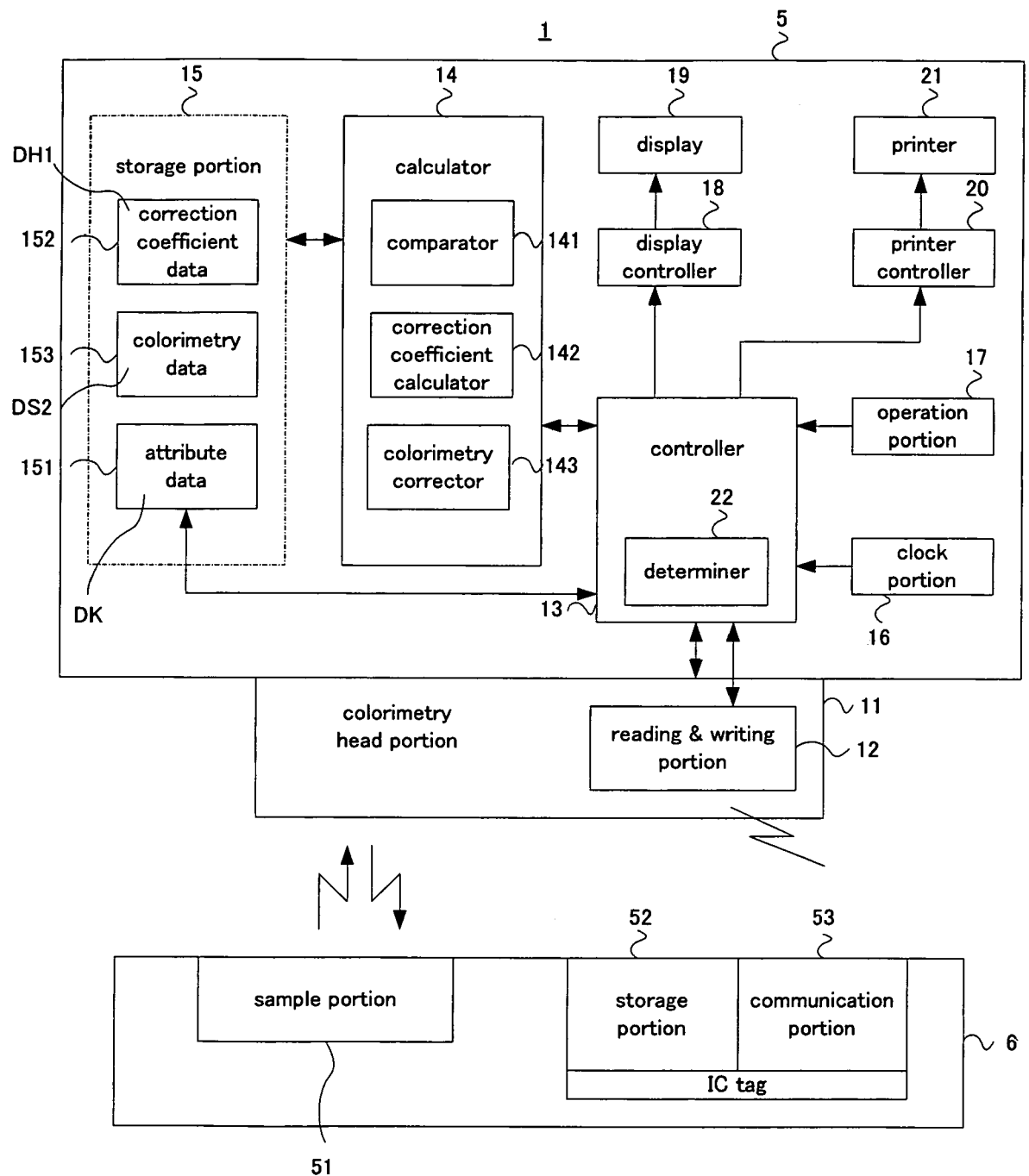
FIG. 2 is a block diagram showing the functional structure of the colorimetry system.
Figure 5:
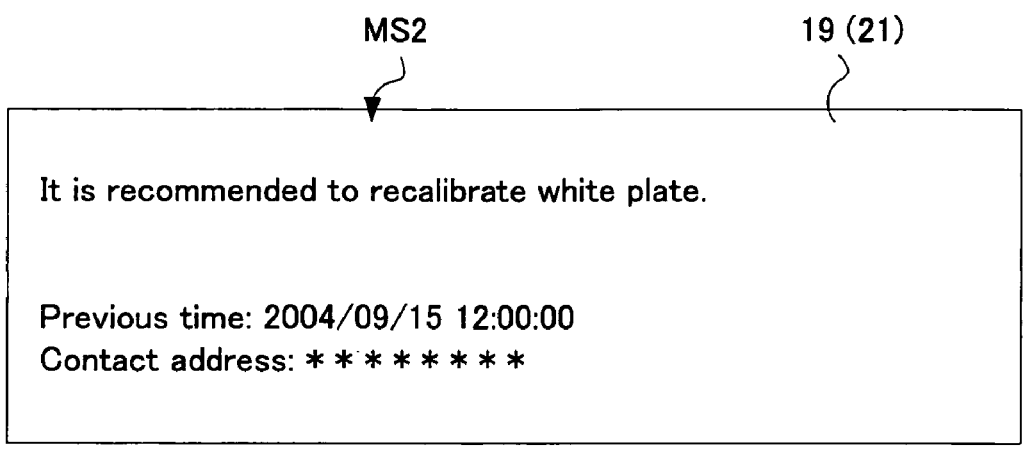
FIG. 5 is a view showing an example of a recalibration urging message.

FIG. 1 is a perspective view showing the appearance of a colorimetry system (optical characteristic measurement system) according to a first embodiment of the present invention. FIG. 2 is a block diagram showing the functional structure of the colorimetry system 1. FIG. 3 is a view showing an example of the data stored in a storage medium of a standard color sample (standard plane sample) 6. FIG. 4 is a view showing an example of a recalibration urging message MS1. FIG. 5 is a view showing an example of a recalibration urging message MS2.

In FIG. 1, the colorimetry system 1 comprises a calorimeter 5 and the standard color sample 6.

The colorimeter 5 of the present embodiment is a portable type that measures the optical characteristic of the standard sample 6 and a sample (object) to be measured. In this example, a spectral type is used. The colorimeter 5 is connected to a non-illustrated personal computer or the like through a cable CB as required, and exchanges data and command signals with the personal computer.

In the present embodiment, the standard color sample 6 is the white place (white sample) used for performing the calibration of the colorimeter 5. The standard color sample 6 is provided with: a sample portion 51 measurement (colorimetry) of which is performed by the calorimeter 5 to supply actual measurement data; a storage portion 52 for storing attribute data DK related to the standard color sample 6; and a communication portion (interface means) 53 for performing data communication with the calorimeter 5 such as transmitting the data stored in the storage portion 52 to the calorimeter 5 or receiving data from the calorimeter 5.

The storage portion 52 is a readable and writable non-volatile storage medium (memory), and is mounted on the standard color sample 6 so as to be integrally fixed thereto. In the present embodiment, as the storage portion 52, an IC tag capable of wireless data transmission and reception is used. Thus, in this case, the communication portion 53 is a radio transmitter, and the radio transmitter is also provided inside the IC tag. The communication portion 53 may perform wired data transmission and reception instead of wireless data transmission and reception. In the case of wired communication, as the communication portion 53, an electric contact such as a connector, an appropriate interface circuit and an electric connector such as a cable are used.

As shown in FIG. 3, various pieces of data are stored as the attribute data DK in the storage portion 52. That is, the following data are stored in the storage portion 52: the sample identifier (identification data) DK1; the sample management number DK2; the shortest wavelength DK3; the wavelength pitch DK4; the number of pieces of data DK5; the measurement temperature DK6; the reflectance calibration data (reference data, calibration data) DK7; and the calibration date (date data) DK8.

The sample identifier DK1 is for identifying the kind of the standard color sample 6 (sample portion 51). In this example, a four-figure decimal number "0000" representative of the white plate (white calibration plate) is stored as the sample identifier DK1. For information, with respect to color samples, the sample identifiers DK are "0001," "0002," etc. Appropriate sample identifiers DK are assigned also to general samples.

The sample management number DK2 is a number for individually identifying the standard color sample 6. In this example, an eight-figure decimal number "01234567" is stored.

The shortest wavelength DK3 and the wavelength pitch DK4 represent the wavelength corresponding to the first piece of data of the reflectance calibration data DK7 and the wavelength pitch corresponding to each piece of data, respectively. In this example, for these, "360" nm and "10" nm are stored, respectively. The number of pieces of data DK5 represents the number of pieces of reflectance calibration data DK7. In this example, "39" pieces of reflectance calibration data DK7 are stored. The measurement temperature DK6 represents the ambient temperature when the reflectance calibration data DK7 is measured.

The reflectance calibration data DK7 is data representing the spectral reflectance, at each wavelength, of the sample portion 51 as a percentage. In this example, "93.35," "95.15," "96.17," "96.98," etc. are stored. For the white plate, it is desirable that the spectral reflectances are all close to "100" and be uniform for all the wavelengths.

The calibration date DK8 is the date on which the reflectance calibration data DK7 is obtained. In this example, measurement is performed at twelve o'clock sharp on Sep. 15, 2004.

The attribute data DK may be partly omitted, or another piece of data may be added.

In FIG. 2, the calorimeter 5 is provided with a colorimetry head portion (colorimetry portion) 11, a reading and writing portion 12, a controller 13, a calculator 14, a storage portion 15, a clock portion 16, an operation portion 17, a display controller 18, a display 19, a printer controller 20, a printer 21, and a determiner 22.

In response to a command from the controller 13, the colorimetry head portion 11 performs colorimetry of various samples such as the standard color sample 6 or an object. The colorimetry value (actual measurement data) DS1 obtained by the colorimetry is transmitted to the calculator 14.

The reading and writing portion 12 is attached in the vicinity of the colorimetry head portion 11, and performs wireless data transmission and reception through the communication portion 53 of the standard color sample 6. By this, the attribute data DK stored in the storage portion 52 is read, and data is transmitted and stored into the storage portion 52. That is, the reading and writing portion 12 has the function of a reader and writer that performs data communication with the IC tag. The attribute data DK read from the storage portion 52 is wholly or partly stored in an attribute data storage portion 151.

The controller 13 controls the calibration processing and other processings to thereby control the overall operation of the calorimeter 5. The white calibration processing is executed when the standard color sample 6 is the white plate.

The calculator 14 performs a calculation on the colorimetry value DS1 measured by the colorimetry head portion 11 to thereby calculate a corrected measurement value DS2, and performs various calculations such as calculating correction coefficient data DH1 from the reflectance calibration data DK7 and the actually measured colorimetry value DS1 of the standard color sample 6.

That is, the calculator 14 is provided with a comparator 141, a correction coefficient calculator 142 and a colorimetry corrector 143. The comparator 141 compares the calorimetry value DS1 obtained by performing the calorimetry of the sample portion 51 by the colorimetry head portion 11 with the reflectance calibration data DK7 when it is recognized that the standard color sample 6 is the white plate based on the sample identifier DK1 read from the storage portion 52.

The correction coefficient calculator 142 generates the correction coefficient data DH1 in the calorimeter 5 based on the-difference between the calorimetry value DS1 and the reflectance calibration data DK7 obtained from the result of the comparison by the comparator 141. The generated correction coefficient data DH1 is stored in a correction coefficient data storage portion 152 of the storage portion 15.

The calorimetry corrector 143 applies the correction coefficient data DH1 to the calorimetry value DS1 obtained by performing the calorimetry of the object, and calculates the corrected calorimetry value DS2. The calculated colorimetry value DS2 is temporarily stored in a calorimetry data storage portion 153. The colorimetry value DS2 stored in the colorimetry data storage portion 153 is outputted to the outside at the appropriate time and displayed on the display 19 or printed by the printer 21.

The storage portion 15 is a readable or writable storage medium or storage area provided in the calorimeter 5. The storage portion 15 is provided with the attribute data storage portion 151, the correction coefficient data storage portion 152, and the colorimetry data storage portion 153 as mentioned above, and data is stored in each of these portions by the control by the controller 13.

The clock portion 16 holds the current time information indicated by year, month, day, hour, minute and second, and transmits the current time information to the determiner 22 in response to a command from the controller 13.

The operation portion 17 is for providing the colorimeter 5 with an operation command and the like and setting the operation mode, and is operable by the user. For example, a trigger signal to start the colorimetry of the sample or start the calibration processing can be supplied by the operation portion 17. Moreover, it is possible to set information to be written into the storage portion 52 of the standard color sample 6 and provide a command to perform writing into the storage portion 52.

The display controller 18 performs the control to display a predetermined image or the like on the display 19 according to the signal from the controller 13. On the display 19, the colorimetry value DS2 obtained by performing the colorimetry of the sample, information on the colorimetry operation, a recalibration urging message described later, and other various pieces of information and images are displayed.

The printer controller 20 controls printing to the printer 21. The printer 21 prints, on sheets of paper, the colorimetry value DS2 obtained by performing the colorimetry of the sample, the recalibration urging message and other various pieces of information.

The determiner 22 determines whether a predetermined period or more has elapsed from the calibration date DK8 read from the storage portion 52 of the standard color sample 6 or not based on the current time from the clock portion 16. While the predetermined period is set to, for example, one year as the initial value, it may be set by the user operating the operation portion 17, and may be set to, for example, two years or three years. When the predetermined period or more has elapsed from the calibration date DK8, the recalibration urging message indicating this is displayed on the display 19 or printed by the printer 21.

Examples of the recalibration urging message are shown in FIGS. 4 and 5. The detailed recalibration urging message MS1 shown in FIG. 4 is displayed, and the abridged recalibration urging message MS2 shown in FIG. 5 is displayed.

Next, the operation of the colorimetry system 1 will be described.

In the present embodiment, the calibration processing performed before the colorimetry of the sample will be described. The calibration processing is absolutely necessary when the colorimeter 5 is used, and is applied in a variety of operations from researches and developments to manufacturing sites.

The calibration processing is performed to suppress the influence of variations in the characteristic of the light source for measurement incorporated in the colorimetry head portion 11 or the influence of the aged deterioration in the reflectance of the inner surface of the integrating sphere of the colorimetry head portion 11. In the calibration processing, the colorimetry of the white plate is performed by the colorimetry head portion 11, and the obtained colorimetry value DS1 is compared with the reflectance calibration data DK7 stored in the attribute data storage portion 151 to calculate the correction coefficient data DH1. For the colorimetry value DS1 of the sample obtained thereafter, the deterioration in measurement accuracy can be suppressed by multiplying it by the calculated correction coefficient data DH1. This will be described below in more detail.

First, the colorimetry will be described. When the colorimetry of the sample is started, the light source for measurement emits light. The light emitted from the light source for measurement is diffusely reflected at the inner wall of the integrating sphere, and uniformly applied to the sample surface. The light reflected at the sample surface is received by a spectral sensor for sample measurement provided on the colorimetry head portion 11. The spectral sensor for sample measurement separates the reflected light from the sample surface into spectral components, and outputs a current corresponding to the intensity of the light to an analog processing circuit. The output from the analog processing circuit is processed by the controller 13 and the calculator 14, thereby obtaining the colorimetry value DS1 which is the spectral reflectance data of the sample. Based on this data, the colorimetry data (colorimetry value DS2) such as L*a*b* or Yxy is derived.

While in this example, diffuse illumination is used as the illumination for measurement and description is given with respect to a geometry of <diffuse illumination/one-way light reception>to observe the measurement surface at a predetermined angle, the present invention is not limited thereto; for example, a different geometry such as <45 illumination/ vertical light reception>may be used.

In the present embodiment, the white plate is prepared as the standard color sample 6. When the colorimetry head portion 11 is brought close for the colorimetry of the standard color sample 6, the reading and writing portion 12 reads the sample identifier DK1 of the attribute data DK of the storage portion 52. The controller 13 determines whether the standard color sample 6 is the white plate or not based on the read sample identifier DK1. When it is determined that the sample 6 is the white plate, the calibration processing is started. When it is determined that the sample 6 is not the white plate, a different processing is performed.

Since the colorimeter 5 is capable of identifying the kind of the sample before the colorimetry as described above, the colorimetry mode can be automatically switched according to the use of the sample. Consequently, in that case, the colorimetry mode switching operation which is conventionally manually performed by the user is unnecessary, so that workability improves. Examples of the colorimetry mode include a calibration mode, a reference color colorimetry mode and a sample colorimetry mode.

When recognizing that the standard color sample 6 is the white plate, the controller 13 reads another piece of attribute data DK stored in the storage portion 52, and stores it into the attribute data storage portion 151. Then, the controller 13 commands the colorimetry head portion 11 to perform the colorimetry of the sample portion 51 of the standard color sample 6. By this, the colorimetry head portion 11 automatically shifts to a calibration execution mode (calibration processing mode). The user can perform the white calibration only by depressing a button of the operation portion 17 or the like provided on the colorimetry head portion 11.

The white calibration processing may be started without the user depressing a button or the like. In particular, in a case where a wired connection is made between the reading and writing portion 12 and the communication portion 53 by-use of a connector or the like so that normal connection is made when the standard color sample 6 is disposed in a predetermined position with respect to the colorimeter 5, since it may be made unnecessary for the user to confirm the disposition of the standard color sample 6, the user's depression of the button may be omitted.

Detecting means for detecting that the standard color sample 6 is set in the predetermined position with respect to the calorimeter 5 may be provided. And the processing is continued only when it is detected that the standard color sample 6 is set in the predetermined position. For example, only when it is determined that the sample 6 is set in the predetermined position, the determination by the determiner 22 and the display by the display controller 18 are performed. As such detecting means, a proximity sensor that operates mechanically, magnetically or optically, or other various sensors may be used. It may be detected that the reading and writing portion 12 and the communication portion 53 are connected together by a connector.

When the calibration is executed, the colorimetry head portion 11 transmits the colorimetry value DS1 of the standard color sample 6 to the calculator 14. Simultaneously therewith, in response to a command from the controller 13, the reflectance calibration data DK7 and the like stored in the attribute data storage portion 151 is transmitted to the calculator 14. In response to a command from the controller 13, the calculator 14 calculates the correction coefficient data DH1 from the colorimetry value DS1 of the standard color sample 6 and the reflectance calibration data DK7.

The correction coefficient data DH1 is obtained as, for example, the value of the ratio of the reflectance calibration data DK7 to the colorimetry value DS1. In this case, for example, when the reflectance calibration data DK7 of a wavelength is "95.00" and the colorimetry value DS1 of the same wavelength is "92.00," the correction coefficient data DH1 of the wavelength is "1.0326" (=95.00/92.00). The correction coefficient data DH1 may be the reciprocal thereof. In this manner, the correction coefficient data DH1 is calculated with respect to all the wavelengths. The calculated correction coefficient data DH1 is stored in the correction coefficient data storage portion 152.

Then, the controller 13 transmits the calibration date DK8 of the attribute data DK to the determiner 22. Simultaneously therewith, in response to a command from the controller 13, the clock portion 16 transmits the current time information to the determiner 22. In response to a command from the controller 13, the determiner 22 compares the calibration date DK8 with the current time information, and determines whether the predetermined period or more has elapsed or not. When it is determined that the predetermined time or more has elapsed, recalibration is urged. When it is determined that the predetermined time has not elapsed, the calibration processing is ended.

Recalibration is urged by displaying the recalibration urging message MS as mentioned above on the display 19 or by printing it by the printer 21.

That is, in response to a command from the controller 13, the determiner 22 transmits a command to display the recalibration urging message MS2 and the calibration date DK8 to the display controller 18 and the printer controller 20. In response to a command from the controller 13, the display controller 18 controls the display 19 to display the recalibration urging message MS1 or MS2. In response to a command from the controller 13, the printer controller 20 confirms the connection of the printer 21, and when communication can be performed normally, controls the printer 21 to print the recalibration urging message MS1 or MS2 as shown in the figure. When the printer 21 is not connected or when there is a problem with the communication with the printer 21, the printing processing of the recalibration urging message MS is discontinued, and the calibration processing is ended.

Next, the operation of the colorimetry system 1 will be described with reference to a flowchart.

Figure 6:
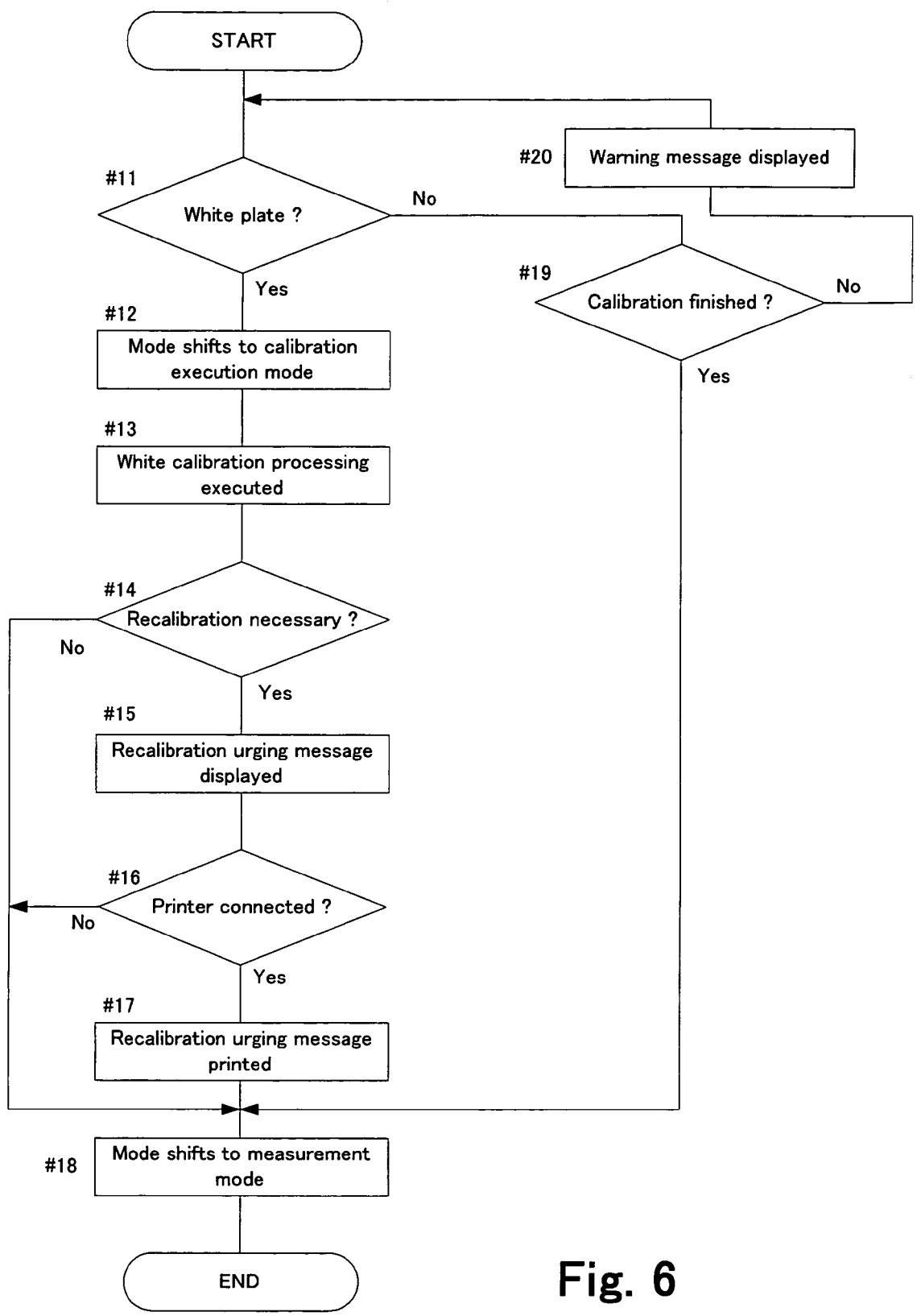
FIG. 6 is a flowchart showing the operation of the colorimetry system.

FIG. 6 is the flowchart showing the operation of the colorimetry system 1.

In FIG. 6, when it is determined that the standard color sample 6 is the white plate based on the sample identifier DK1 read from the storage portion 52 by the reading and writing portion 12 (YES of #11), the mode shifts to the calibration execution mode (#12), and the white calibration processing is executed (#13). The white calibration processing is started by the user depressing the execution button thereof. The correction coefficient data DH1 is obtained by the white calibration processing.

Whether the white recalibration is necessary or not is determined (#14). This determination is made based on the calibration date DK8 read from the storage portion 52 and the current time as mentioned above. When it is necessary (YES of #14), the recalibration urging message MS is displayed on the display screen of the display 19 (#15). The connection of the printer 21 is confirmed (#16), and the recalibration urging message MS is printed by the printer 21 (#17). Then, the mode shifts to a measurement mode (#18).

When the standard color sample 6 is not the white plate at step #11, whether the calibration (user calibration) has been finished or not is determined (#19). When the calibration has been finished (YES of #19), the mode shifts to the measurement mode (#18). When the calibration has not been finished (NO of #19), a warning message indicating this is displayed on the display screen of the display 19 (#20).

According to the colorimetry system 1 of the above-described embodiment, since the sample portion 51 and the storage portion 52 storing the attribute data DK thereof are integrally provided in the standard color sample 6, these portions are never separated from each other. Since the attribute data DK is stored in the storage portion 52 provided integrally with the sample portion 51 and further, the communication portion 53 is integrally provided, the calorimeter 5-can easily read the attribute data DK through the reading and writing portion 12. For example, it is possible to automatically read the attribute data DK by setting the standard color sample 6 in the colorimeter 5 for measurement.

Moreover, since the calibration date DK8 is stored in the storage portion 52 of the standard color sample 6 and when the predetermined period has elapsed, the recalibration urging message MS is issued based on the calibration date DK8, this makes the user notice that the calibration (manufacturer calibration, that is, confirmation of the reflectance value or value re-assignment as required) of the standard color sample 6 is necessary, and an opportunity to perform the calibration can be seized. This prevents the colorimeter 5 from being used without the calibration of the standard color sample 6 being performed for a long period.

As described above, according to the colorimetry system 1 of the present embodiment, the usability of the calorimeter 5 and the standard color sample 6 is improved.

While in the above-described first embodiment, an example of application to a colorimetry system is shown as the optical characteristic measurement system according to the present invention, the present invention is absolutely similarly applicable to the gloss measurement system.

In the case of the gloss measurement system, as described in JIS-Z-8741-1997 "Specular glossiness—Method of measurement," as the reference of the specular glossiness, "The specular glossiness Gs (θ) at a defined incident angle θ on a glass surface where the refractive index is fixed at 1.567 over all wavelengths in the visible region is used as the reference, and the specular glossiness is expressed with this value as 100%." Specifically, for the primary standard plane of the specular glossiness, a smooth plane such as transparent or black glass is used as the primary standard plane of the specular glossiness at the defined incident angle θ, and the specular glossiness is determined by a predetermined method. Moreover, as the practical standard plane of the specular glossiness, an opal glass plane having various specular glossinesses, a white tile plane, or a plane made of the same material as the sample according to various objects is used, and the practical standard plane must be calibrated with respect to the primary standard plane of the specular glossiness.

That is, the primary standard plane or the practical standard plane of the specular glossiness in the gloss measurement can be said to correspond to the standard white sample in the colorimetry system. Moreover, the gloss specimen sample in the gloss measurement system corresponds to the color specimen sample in the colorimetry system.

Second Embodiment

In the second embodiment, an example of a system for accurately and efficiently managing and using a variety of color samples will be described. In particular, the creation and calibration (update) of the color sample management information will be described.

Generally, the pass/fail judgments of products manufactured at factories and the like are frequently made both based on the color values and by visual inspection. When the pass/fail judgment is made based on the color value, the color value obtained by performing the colorimetry of the color sample by the calorimeter is used as the reference color. With respect to the reference color, a management range permissible for the color value of the product is set. For the management range, for example, a predetermined deviation management range for each of L*, a* and b* of the reference color is set as the permissible value. Moreover, it may be set by an absolute value. The pass/fail judgment is made based on whether the color difference between the color value obtained by performing the colorimetry of the product by the calorimeter and the reference color is within the management range or not.

Moreover, when the pass/fail judgment is made by visual inspection, in addition to the color sample, an upper limit sample and a lower limit sample are used as judgment criteria. The worker compares the product with each sample with the eye, and makes the pass/fail judgment based on whether the color of the product is between the colors of the upper limit and lower limit samples or not.

The color sample management information of the color sample differs according to the product and use. Materials of the color sample vary widely, and some are readily browned or discolored with time and some are not. The difference in color sample management information affects the color value, and the browning or the discoloration affects the visual inspection.

The color sample management information includes the sample identifier, the color sample name, the user calibration (colorimetry) date, the management range (or the limit value), the reflectance deviation range (the allowance value of the degree of browning or discoloration), the reflectance (color sample) data, the colorimeter-information (the type of the colorimeter, the illumination light reception optical system, etc.), the colorimetry condition (the measurement diameter, the regularly reflected light processing, the UV condition), and the observation condition (the visual field, the light source).

In the second embodiment, an example is shown of a system for accurately and efficiently managing and using the color sample that is important in performing the pass/fail judgment of the product, without any influence of the difference in color sample management information and the browning or the discoloration. Specifically, an example will be described in which the color sample management information is inputted to the IC tag provided on the color sample. In the second embodiment, the structure, function and the like of each element will be described with reference mainly to the difference from those of the first embodiment. The parts not described in the second embodiment may be considered as substantially similar to those of the first embodiment.

Figure 7:
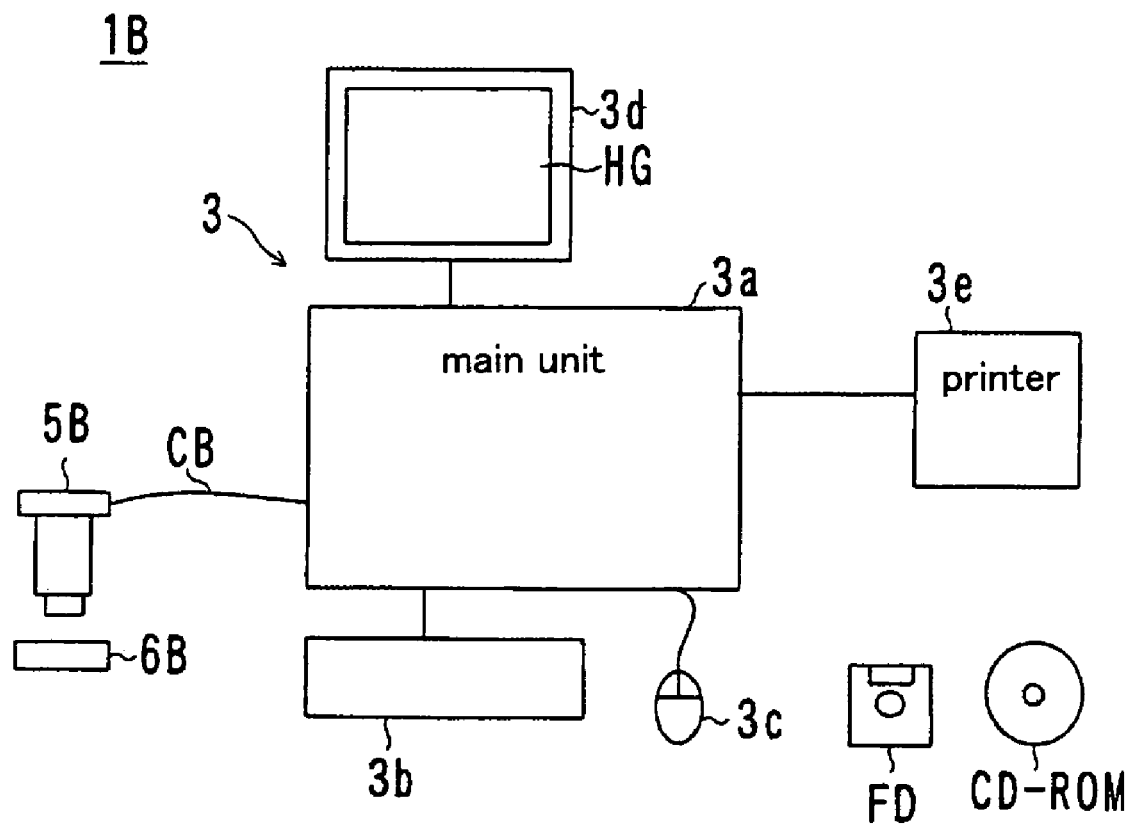
FIG. 7 is a view showing the appearance of a colorimetry system according to a second embodiment of the present invention.
Figure 8:
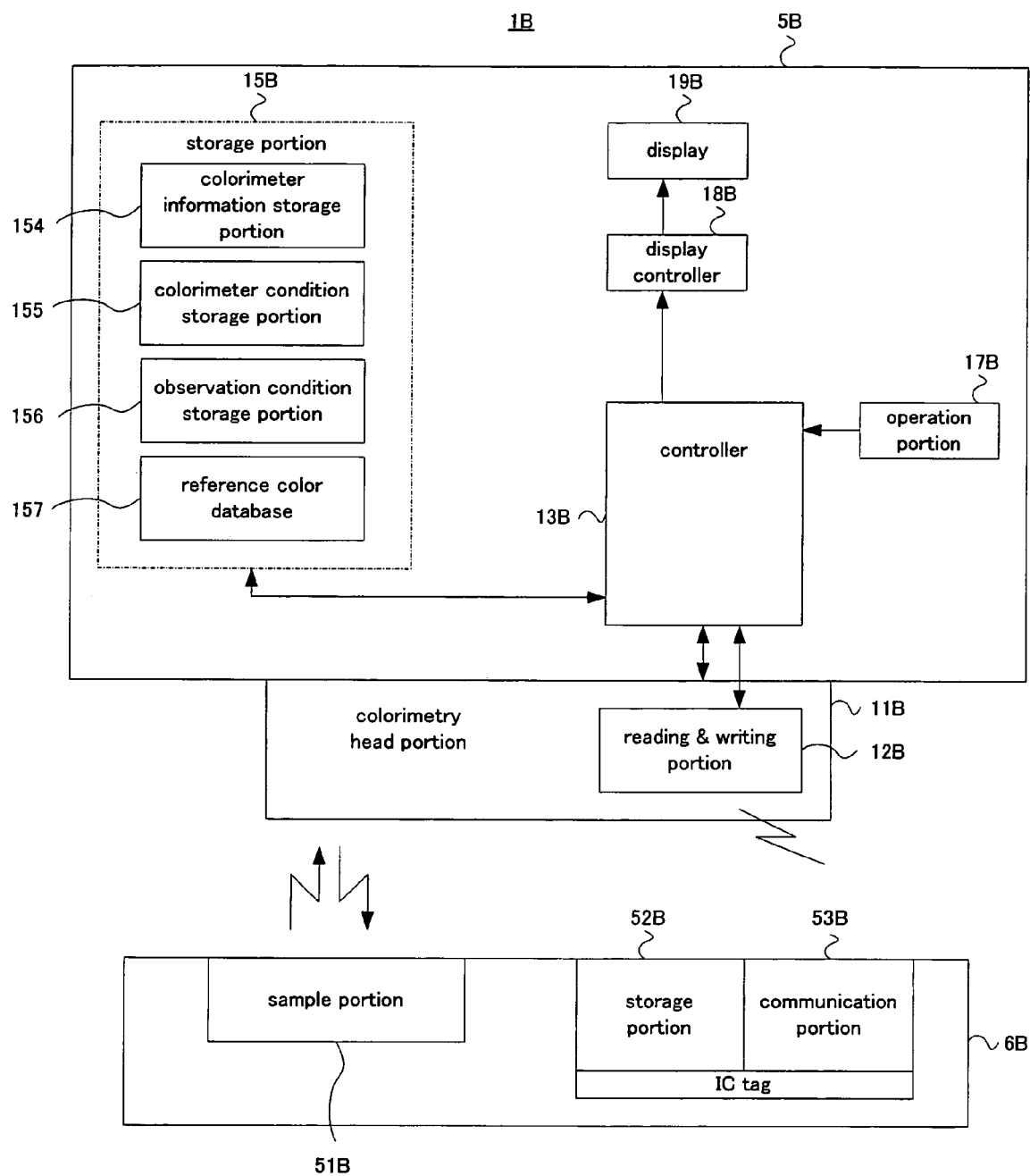
FIG. 8 is a block diagram showing the functional structure of the colorimetry system.
Figures 11, 12:
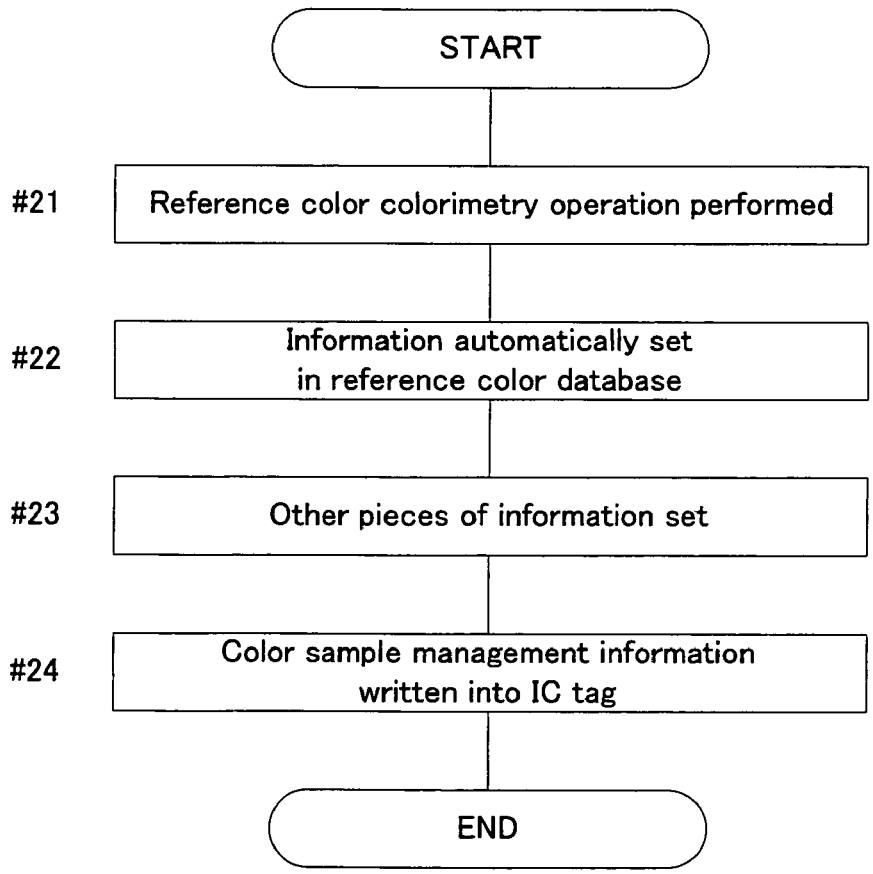
FIG. 11 is a view showing an example of a management range setting screen.
FIG. 12 is a flowchart showing the operation of the colorimetry system according to the second embodiment.

FIG. 7 is a view showing the appearance of a colorimetry system 1B according to the second embodiment of the present invention. FIG. 8 is a block diagram showing the functional structure of the colorimetry system 1B. FIG. 9 is a view showing an example of the data stored in a storage medium of a standard color sample 6B. FIG. 10 is a view showing an example of a colorimetry trigger screen HG1. FIG. 11 is a view showing an example of a management range setting screen HG2. 114 As shown in FIG. 7, in the second embodiment, the colorimetry system 1B comprises a computer system 3, a colorimeter 5B and the standard color sample 6B.

The computer system 3 comprises a main unit 3a, input devices such as a keyboard 3b and the mouse 3c, a display 3d and a printer 3e. As such a computer system 3, a personal computer, a workstation or the like may be used.

The main unit 3a includes a CPU, a memory such as a ROM or a RAM, a hard disk device, various drive devices, a communication interface, various peripheral devices and a control circuit. On the hard disk device, various files and databases are stored. These databases are transferred and copied between the hard disk device and the memory. Moreover, on the hard disk device, support software for supporting the operation of the calorimeter 5B, software for the optical measurement and optical characteristic management of various products which are the objects (color management software) and the like are installed. These pieces of software are read into the memory as appropriate, and executed by the CPU. In the memory, various parameters, arithmetic expressions and the like are stored as required. Moreover, the main unit 3a is connected to an external network by a network interface, so that the transmission and the reception of various programs and data are possible. Moreover, the main unit 3a is provided with a media drive, so that the access to recording media such as a flexible disk FD, a CD-ROM, a magneto-optical disk, a memory chip and a memory card is possible.

The key board 3b and the mouse 3c are used for the user to provide various instructions and commands on the screen displayed on the display screen HG of the display 3d, and also used for the user to input various pieces of data or provide commands to the main unit 3. On the display screen HG of the display 3d, the colorimetry trigger screen HG1 and the management range setting screen HG2 described later are displayed and also, various pieces of data, characters or images are displayed.

The calorimeter 5B used in the second embodiment may be the same as the calorimeter 5 used in the first embodiment or may be different therefrom. For example, it may be a bench top type. The colorimeter 5B is connected to the main unit 3a of the computer system 3 through the cable CB.

The standard color sample 6B is a color sample used for determining whether the product which is the object is normally manufactured or not (pass/fail judgment). This is also called a standard sample or a limit sample. While the standard color sample 6B has a sample portion 51B, a storage portion 52B and a communication portion 53B like the first embodiment, the contents thereof are partly different. Details will be described below.

As shown in FIG. 9, in the storage portion 52B, the following are stored as the attribute data DK: the sample identifier DK11, the color sample name DK12, the measurement date DK13, the management range DK14, the reflectance deviation range DK15, the shortest wavelength DK16, the wavelength pitch DK17, the number of pieces of data DK18, the measurement temperature DK19, the (reference data) DK20, the colorimeter type DK21, the body number DK22, the colorimeter version DK23, the measurement method DK24, the illumination light reception optical system DK25, the measurement diameter DK26, the regularly reflected light processing DK27, the UV condition DK28, the visual field DK29, and the light source DK30. These pieces of attribute data DK are written into the storage portion 52B at the time of the manufacture of the standard color sample 6B. At the time of the calibration, the attribute data DK is written into the storage portion 52B by the colorimeter 5B.

The reflectance data DK20 is data representing, as a percentage, the spectral reflectance at each wavelength of the sample portion 51B of the standard color sample 6B which is a color sample. The pieces of attribute data DK21 to DK30 from the colorimeter type DK21 to the light source DK30 are the measurement conditions.

Of these pieces of attribute data DK, the color sample name DK12, the management range DK14 and the reflectance deviation range DK15 can be manually set by the user from a predetermined screen. The visual field DK29 and the light source DK30 can be selected by the user from among a plurality of pieces of information. As the reflectance data DK20, the actually measured reflectance data is automatically set. As the measurement date DK13, the date on which the colorimetry is performed is automatically set.

In FIG. 8, the calorimeter 5B is provided with a colorimetry head portion (measuring portion) 11B, a reading and writing portion 12B, a controller 13B, a storage portion 15B, an operation portion 17B, a display controller 18B, and a display 19B.

Based on the reference color colorimetry operation by the operation portion 17, the controller 13 issues a colorimetry command, and the colorimetry head portion 11B performs the colorimetry of the standard color sample 6B and various other samples or the product which is the object. The colorimetry value DS1 obtained by the colorimetry is transmitted to the controller 13B.

The reading and writing portion 12B is attached in the vicinity of the colorimetry head portion 11B, and performs wireless signal transmission and reception through the communication portion 53B of the standard color sample 6B. By this, the attribute data DK stored in the storage portion 52B is read, and data is transmitted and written into the storage portion 52B. That is, the reading and writing portion 12B has the function of a reader and writer that performs data communication with the IC tag.

The signal transmission and reception is not limited to wireless transmission and reception. It may be wired data transmission and reception through an electric connector.

The storage portion 15B is provided with a colorimeter information storage portion 154, a calorimeter condition storage portion 155, an observation condition storage portion 156 and a reference color database 157.

In the calorimeter information storage portion 154, the colorimeter type DK21, the body number DK22, the colorimeter version DK23, the measurement method DK24 and the illumination light reception optical system DK25 are stored. The measurement method DK24 is reflection, transmission or the like.

In the calorimeter condition storage portion 155, the measurement diameter DK26, the regularly reflected light processing DK27 and the UV condition DK28 are stored. The regularly reflected light processing DK27 represents whether the regularly reflected light from the sample surface is included (SCI: specular component included) or excluded (SCE: specular component excluded). The UV condition DK28 represents the presence or absence of UV components of excitation light at the time of the fluorescent sample measurement.

In the observation condition storage portion 156, the visual field DK29 and the light source DK30 are stored. The visual field DK29 is, for example, a visual field of 20 or a visual field of 100. The light source DK30 is, for example, a standard illuminant A or D65.

In the reference color database 157, the sample identifier DK11, the color sample name DK12, the measurement date DK13, the management range DK14, the reflectance deviation range DK15, the shortest wavelength DK16, the wavelength pitch DK17, the number of pieces of data DK18, the measurement temperature DK19 and the reflectance data DK20 are stored.

The operation portion 17B is for providing the calorimeter 5B with an operation command and setting the operation mode. For example, a trigger signal to start the colorimetry of a sample or the standard color sample 6B is supplied by the operation portion 17B. Moreover, it is possible to set the information written into the storage portion 52B of the standard color sample 6B and provide a command to write it into the storage portion 52B. In response to a command from the controller 13B, the display controller 18B displays the colorimetry trigger screen HG1 on the display 19B.

Next, the operation of the colorimetry system 1B will be described. In the following, the processing will be described to write the color sample management information of the standard color sample 6B into the storage portion 52B of the IC tag by the calorimeter 5B.

By the user performing a reference color colorimetry operation by operating the operation portion 17B while viewing the display 19B, the controller 13B provides a colorimetry command, and the colorimetry of the standard color sample 6B set on the colorimetry head portion 11B is performed. The controller 13B sets the reflectance data of the standard color sample 6B obtained by the actual measurement by the colorimetry head portion 11B and the measurement date in the reference color database 157 as the reference color data (the reflectance data DK20 and the measurement date DK13).

When such setting and series of processings associated with the colorimetry are completed, the user inputs information such as the color sample name DK12 and the management range DK14 from the operation portion 17B while viewing the display 19B. The inputted information is set in the reference color database 157.

When the setting of all the pieces of information to be inputted to the reference color database 157 is finished, the user executes the setting processing for writing the color sample management information into the storage portion 52B of the IC tag by operating the operation portion 17B while viewing the display 19B.

The controller 13B first reads the color sample management information to be written into the IC tag, from the calorimeter information storage portion 154, the calorimeter condition storage portion 155, the observation condition storage portion 156 and the reference color database 157. Then, the controller 13B commands the reading and writing portion 12B to write the read color sample management information (the colorimeter information, the calorimeter condition, the observation condition, the reference color database information) into the IC tag.

In the present embodiment, the operation portion by the software as shown in FIG. 10, that is, the colorimetry trigger screen HG1 is displayed on the display screen HG of the display 3d of the computer system 3. By a click on a reference color measurement button BT11 on the colorimetry trigger screen HG1, the controller 13B commands the colorimetry head portion 11B to perform the colorimetry of the standard color sample 6B which is a color sample.

For information, when the calorimeter 5B is not connected to the computer system 3, after the user performs a predetermined operation on the operation portion 17B while viewing the display 19B so that the colorimetry of the reference color can be performed, the colorimetry of the standard color sample 6B is performed.

Moreover, the management range setting screen HG2 as shown in FIG. 11 is displayed on the display screen HG of the display 3d. On the management range setting screen HG2 shown in FIG. 11, the upper limit and the lower limit can be set with respect to $\Delta L^*$, $\Delta a^*$ and $\Delta b^*$, and the upper limit can be set with respect to $\Delta E^*ab$. Moreover, whether the determination with respect to $\Delta L^*$, $\Delta a^*$, $\Delta b^*$ or $\Delta E^*ab$ is performed or not can also be set. The above description is given with a $L^*a^*b^*$ calorimetric system as an example, other calorimetric systems (a Yxy colorimetric system, a $L^*u^*v^*$ colorimetric system, etc.) may be performed.

Subsequently, the operation of the above-described colorimetry system 1B will be described with reference to the flowchart.

FIG. 12 is a flowchart showing the operation of the colorimetry system 1B.

First, the standard color sample 6B is set in the colorimeter 5B having undergone the white calibration, and when the reference color colorimetry operation is performed on the operation portion 17B, the colorimetry processing is started (#21). When the colorimetry processing is performed, the actually measured value of the reflectance (the colorimetry value DS2) of the sample portion 51B of the standard color sample 6B is obtained.

Then, the colorimetry value DS2 is automatically set in the reference color database 157 as the reference color (#22) The other pieces of information are set in the reference color database 157 (#23). Then the color sample management information is written into the storage portion 52B of the IC tag (#24).

The color sample management information written in the IC tag is rewritten as required. When the color sample management information is not stored in the IC tag yet, the color sample management information is newly written at step #24.

According to the colorimetry system 1B of the second embodiment, the standard color sample which is one of a variety of color samples and the reference data are integrally managed and these can be accurately and efficiently managed and used, so that the usability of the standard color sample is improved.

Third Embodiment

In the third embodiment, an example of a system for performing the colorimetry of the color sample will be described. That is, in the third embodiment, a standard color sample 6C the same as the standard color sample 6B created or calibrated in the second embodiment is used, and data is obtained by performing the colorimetry of a sample portion 51C thereof.

In the third embodiment, the structure, function and the like of each element will be described with reference mainly to the difference from those of the second embodiment. The parts not described in the third embodiment may be considered as substantially similar to those of the second embodiment. The third embodiment and the second embodiment are the same colorimetry systems, and can be considered to be different only in the contents of the processings thereof.

Figure 13:
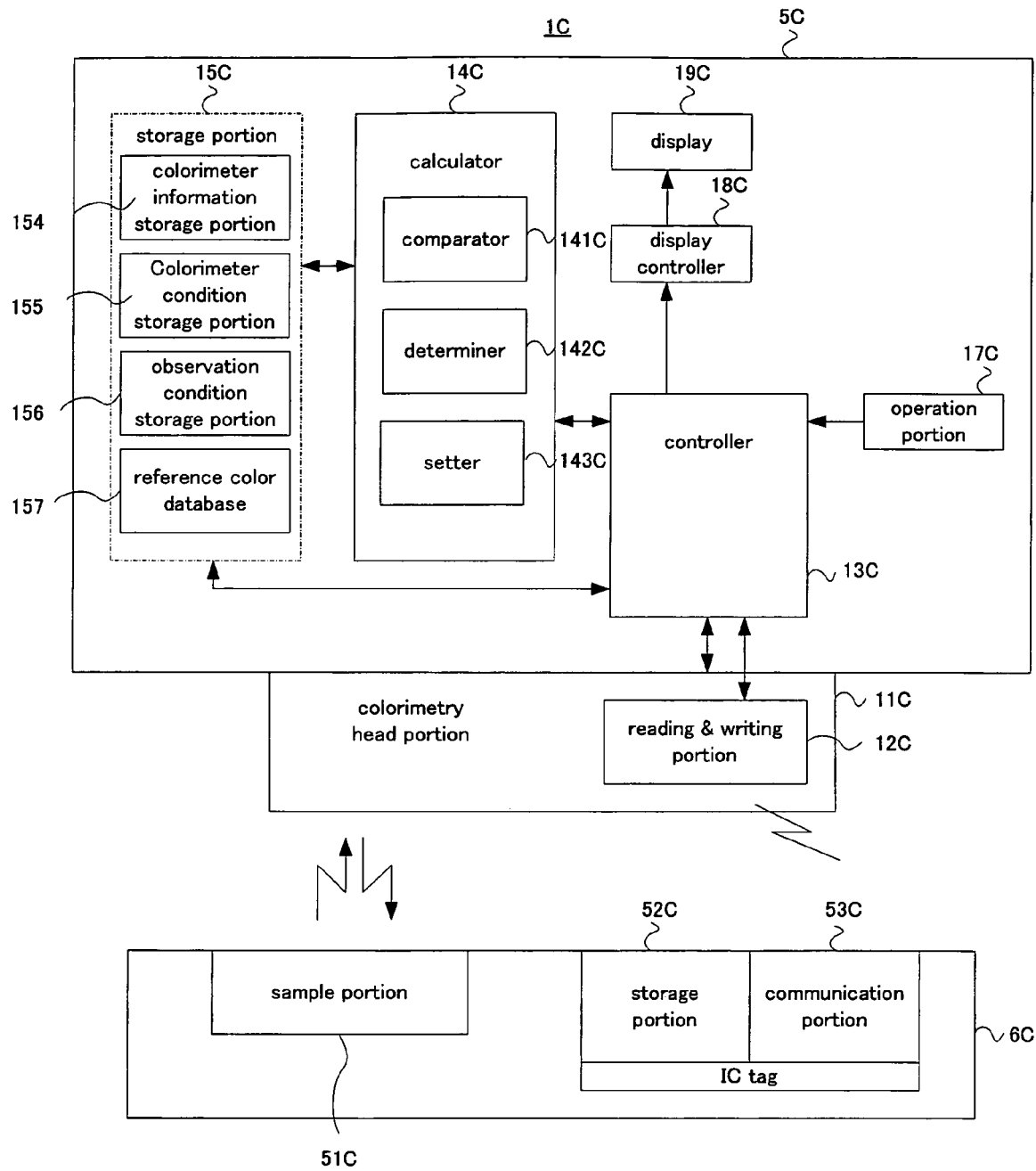
FIG. 13 is a block diagram showing the functional structure of a colorimetry system according to a third embodiment.
Figure 14:
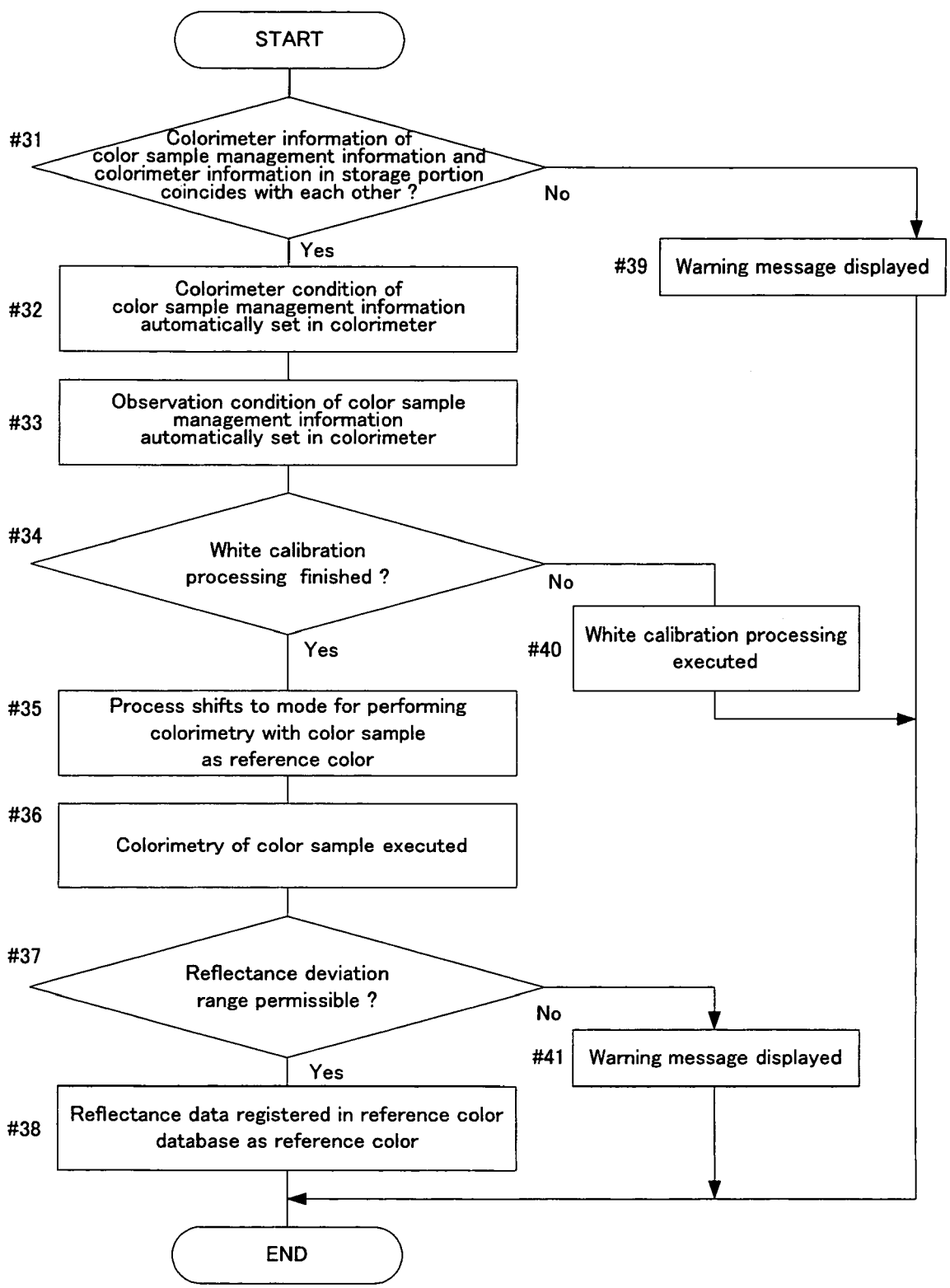
FIG. 14 is a flowchart showing the operation of the colorimetry system according to-the third embodiment.

FIG. 13 is a block diagram showing the functional structure of the colorimetry system 1C according to the third embodiment of the present embodiment. FIG. 14 is a flowchart showing the operation of the colorimetry system 1C.

In FIG. 13, a calorimeter 5C is provided with a calculator 14C. The calculator 14C is provided with a comparator 141C, a determiner 142C and a setter 143C.

In response to a command from a controller 13C, the calculator 14C, particularly, the comparator 141C and the determiner 142C confirm whether or not the colorimeter information stored in the colorimeter information storage portion 154 of the colorimeter 5C coincides with the colorimeter information of the color sample management information read from a storage portion 52C of the standard color sample 6C. The result of the confirmation is transmitted to the controller 3C. When the information coincides, the process shifts to the next processing, and when the information does not coincide, a warning message is displayed on a display 19C through the display controller 18C.

Moreover, the calculator 14C calculates the range of deviation between the reflectance data DK20 of the color sample management information read from the storage portion 52C of the standard color sample 6C and the reflectance data obtained by actually performing the colorimetry of the sample portion 51C, and confirms whether it is within the reflectance deviation range of the color sample management information or not.

When the range of deviation between the reflectance data DK20 and the actually measured reflectance data is within the reflectance deviation range, the actually measured reflectance data is set in the reference color database 157 by the setter 143C, and in the succeeding processing, the reflectance data is used as the reference color data.

Moreover, instead of setting the actually measured reflectance data as the reference color data, the reflectance data DK20 read from the storage portion 52C may be set as the reference color data. Alternatively, the value intermediate therebetween may be set as the reference color data.

In response to a command from the controller 13C, the display controller 18C performs control so that a warning message or the colorimetry trigger screen HG1 is displayed on the display 19C.

Next, the overall operation of the colorimetry system 1C will be described. In the description that follows, it is assumed that the color sample management information is written in the storage portion 52C of the IC tag by the processing in the second embodiment.

The calorimeter 5C reads the color sample management information from the IC tag in the vicinity of the standard color sample 6C. When the sample identifier DK11 is identified as a color sample, the colorimetry processing of the color sample is performed.

First, it is confirmed whether or not the calorimeter information of the color sample management information is the same as the calorimeter information stored in the calorimeter information storage portion 154. When it is the same, the processing is continued, and when it is not the same, the processing is discontinued and a warning message is displayed on the display 19C. As the warning message, for example, what is different between the colorimeter information of the color sample management information and the calorimeter 5C is shown.

When the processing is continued, the colorimetry condition and the observation condition of the color sample management information are automatically set (stored) in the calorimeter condition storage portion 155 and the observation condition storage portion 156 of the calorimeter 5C, respectively.

When the white calibration is necessary, the process shifts to the white calibration processing as shown by the flowchart of FIG. 6, the standard color sample 6C which is the white plate is set on the colorimetry head portion 11C, and the white calibration is executed.

When the white calibration is unnecessary, the process shifts to a mode to perform the colorimetry with the standard color sample 6C as the reference color of the colorimeter 5C, and the colorimetry of the standard color sample 6C set on the colorimetry head 5C is executed.

After the colorimetry is executed, the reflectance data obtained by the colorimetry is compared with the reflectance data DK20 stored as the color sample management information, and it is determined whether the deviation of the reflectance is within a predetermined range, that is, within the reflectance deviation range of the color sample management information or not. When it is not within the range as the result of the determination, a warning message is displayed on the display 19C. When it is within the range, the processing is continued, and the reflectance data obtained by the-colorimetry is automatically set in the reference color database 157 of the calorimeter 5C as the reference color. For the reference color, the color sample name, the management range and the like of the color sample management information are automatically set.

In FIG. 14, the colorimeter information which is a piece of color sample management information and the calorimeter information stored in the calorimeter information storage portion 154 are compared with each other (#31). When these coincide with each other (YES of #31), the calorimeter condition and the observation condition of the color sample management information are automatically set in the colorimeter 5C (#32, #33). On the other hand, the calorimeter information which is a piece of color sample management information and the colorimeter information stored in the calorimeter information storage portion 154 does not coincide with each other (NO of #31), a warning message indicating this is displayed on the display screen of the display 19C (#39).

When the white calibration of the calorimeter 5C is finished (YES of #34), the process shifts to a mode to perform the colorimetry with the standard color sample 6C as the reference color of the calorimeter 5C (#35), and the colorimetry is executed (#36). While, when the white calibration of the calorimeter 5C is not finished (NO of #34), the white calibration is executed (#40).

It is determined whether the deviation between the reflectance data obtained by the colorimetry and the reflectance data DK20 stored as the color sample management information is within the reflectance deviation range or not (#37). When the result is YES at step #37, the reflectance data obtained by the colorimeter is registered in the reference color database 157 (#38). On the other hand, the result is NO at step #37, a warning message indicating this is displayed on the display screen of the display 19C (#41).

In any of the above-described embodiments, as the function implementing method and the function sharing method in the calorimeters 5, 5B and 5C, various methods may be adopted. That is, for example, as the structures and functions of the controller 13, the calculator 14, the storage portion 15 and the like, various structures and functions are adoptable as well as the above-described ones. In brief, it is necessary only that the above-described functions are implemented by software or hardware, or by a combination thereof.

While an example using a-spectral calorimeter is described in all of the above-described embodiments, it is to be noted that the present invention is similarly applicable to a trichromatic direct-reading calorimeter. Moreover, the present invention is applicable not only to normal colorimeters but also to optical measuring devices that require calibration using a reference sample, for example, glossmeters.

The structure, construction, configuration, processing contents, processing method, processing timing and the like of the whole or each part of the above-described colorimetry systems 1, 1B and 1C may be changed as appropriate according to the purport of the present invention.

According to the present invention, the usability of the standard plane surface of the optical characteristic measuring device such as a calorimeter is improved. According to the present invention, a miscombination of the sample and the reference data never occurs, so that an error can be surely avoided that an optical characteristic measuring device is calibrated by use of a wrong reference sample not corresponding to the reference data (calibration data) stored in the optical characteristic measuring device. Moreover, the reading of the reference data into the optical characteristic measuring device can be easily performed. Further, an opportunity to perform the calibration (manufacturer calibration) of the standard plane sample is provided, so that it is avoided that a condition where no manufacturer calibration is performed continues.

Although the present invention has been fully described by way of examples with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A standard plane sample for supplying an optical characteristic measuring device with reference data, comprising:
   a sample portion that is measured by the optical characteristic measuring device to supply measurement data; and
   a recording medium that stores identification data for identifying a kind of the sample portion as well as reference data corresponding to an optical characteristic of said sample portion.

2. The standard plane sample as claimed in claim 1, further comprising:
   a communication portion that performs data communication with the optical characteristic measuring device, and transmits data stored in the recording medium to the optical characteristic measuring device.

3. The standard plane sample as claimed in claim 1, wherein the recording medium stores data for date on which the reference data is obtained.

4. The standard plane sample as claimed in claim 1, wherein the recording medium includes an IC tag.

5. The standard plane sample as claimed in claim 2, wherein the communication portion performs radio data transmission with the optical characteristic measuring device.

6. The standard plane sample as claimed in claim 2, wherein the communication portion performs wired data transmission with the optical characteristic measuring device.

7. An optical characteristic measurement system for measuring an optical characteristic of an object, comprising:
   a standard plane sample comprising:
      a sample portion that is measured by an optical characteristic measuring device to supply measurement data;
      a recording medium that stores identification data for identifying a kind of the sample portion as well as reference data corresponding to an optical characteristic of the sample portion; and
      a communication portion that performs data transmission with the optical characteristic measuring device; and
   the optical characteristic measuring device comprising:
      a measuring portion that measures the object;
      a reading and writing portion that performs data transmission with the standard plane sample through the communication portion of the standard plane sample, and receives data stored in the recording medium of the standard plane sample from the communication portion of the standard plane sample;
      a sample data storage portion that stores the data received by the reading and writing portion;
      a comparator that compares, when it is determined that the standard plane sample is a standard plane sample for calibration based on the identification data, measurement data obtained upon measuring the sample portion of the standard plane sample by the measuring portion with the reference data received from the standard plane sample;
      a correction coefficient calculator that generates correction coefficient data based on a difference between the measurement data of the sample portion and the reference data; and
      a measurement corrector that generates corrected measurement data by applying the correction coefficient data on the measurement data obtained upon measurement of the object by the measuring portion.

8. An optical characteristic measurement system for measuring an optical characteristic of an object, comprising:
   a standard plane sample comprising:
      a sample portion that is measured by an optical characteristic measuring device to supply measurement data;
      a recording medium that stores reference data corresponding to an optical characteristic of the sample portion as well as data for date on which the reference data is obtained; and
      a communication portion that performs data transmission with the optical characteristic measuring device; and
   the optical characteristic measuring device comprising:
      a measuring portion that measures the object;
      a reading and writing portion that performs data transmission with the standard plane sample through the communication portion of the standard plane sample, and receives data stored in the recording medium of the standard plane sample from the communication portion of the standard plane sample;
      a sample data storage portion that stores the data received by the reading and writing portion;
      a determiner that determines whether a predetermined period or more has elapsed from the date represented by the date data received from the standard plane sample; and
      a controller that give a notification when the determiner determines that the predetermined time or more has elapsed.

9. The optical characteristic measurement system as claimed in claim 8, further comprising:
   a display that is controlled by the controller to display that the predetermined time or more has elapsed.

10. The optical characteristic measurement system as claimed in claim 8, further comprising:
    a printer that is controller by the controller to print that the predetermined time or more has elapsed.

11. The optical characteristic measurement system as claimed in claim 8, further comprising:
    a detector that detects the standard plain sample is set in a predetermined position with respect to the optical characteristic measurement device.

12. The optical characteristic measurement system as claimed in claim 8, further comprising:
    an operation portion provided in the optical characteristic device, and that sets data regarding the predetermined period and inputs a command to write that data into the recording medium of the standard plane sample;
    wherein the reading and writing portion writes the data regarding the predetermined period into the recording medium through the communication portion of the standard plane sample in response to the command input from the operation portion.

13. An optical characteristic measurement system for measuring an optical characteristic of an object, comprising:
    a standard plane sample comprising:
       a sample portion that is measured by an optical characteristic measuring device to supply measurement data;
       a recording medium that stores a first optical characteristic device information for specifying the optical characteristic device used with the standard plane sample as well as reference data corresponding to an optical characteristic of the sample portion; and a communication portion that performs data transmission with the optical characteristic measuring device; and the optical characteristic measuring device comprising:

a measuring portion that measures the object;

a reading and writing portion that performs data transmission with the standard plane sample through the communication portion of the standard plane sample, and receives data stored in the recording medium of the standard plane sample from the communication portion of the standard plane sample;

an optical characteristic information storage portion that stores a second optical characteristic device information for specifying the optical characteristic device;

a comparator that compares the first optical characteristic device information received from the recording medium through the communication portion and the second optical characteristic device information stored in the optical characteristic information storage portion;

a controller that controls the measuring portion to measure the optical characteristic data of the sample portion when it is determined that the first optical characteristic device information coincides with the second optical characteristic device information by the comparator; and a determiner that determines whether a difference between the measurement data of the sample portion and the reference data received from the recording medium by the reading and writing portion is within a predetermined deviation range, and the controller gives a notification when it is determined that the difference is not within the predetermined deviation range by the determiner.

14. The optical characteristic measurement system as claimed in claim 13, wherein the controller gives a notification in a display when the difference is not within the predetermined deviation range by the determiner.

15. The optical characteristic measurement system as claimed in claim 13, further comprising:

a setting portion that sets the measurement data of the sample portion or the reference data as reference color data.

16. The optical characteristic measurement system as claimed in claim 13, wherein the controller gives a notification when it is determined that the first optical characteristic device information does not coincide with the second optical characteristic device information by the comparator.

17. The optical characteristic measurement system as claimed in claim 13, further comprising:

an operation portion provided in the optical characteristic device, and that sets data regarding the predetermined deviation range and inputs a command to write the data into the recording medium of the standard plane sample;

wherein the reading and writing portion writes the data regarding the predetermined deviation range into the recording medium through the communication portion in response to the command input from the operation portion.

18. The optical characteristic measurement system as claimed in claim 13, wherein the optical characteristic device includes a spectral colorimeter, a trichromatic direct-reading calorimeter and a glossmeter.

* * * * *